United States Patent [19]

Finkelstein et al.

[11] Patent Number: 4,628,059
[45] Date of Patent: Dec. 9, 1986

[54] DOPAMINE-β-HYDROXYLASE INHIBITORS

[75] Inventors: Joseph A. Finkelstein, Philadelphia, Pa.; Carl Kaiser, Haddon Heights; Lawrence I. Kruse, Haddonfield, both of N.J.

[73] Assignee: SmithKlein Beckman Corporation, Philadelphia, Pa.

[21] Appl. No.: 793,513

[22] Filed: Oct. 31, 1985

[51] Int. Cl.[4] .................. A61K 31/41; C07D 249/08
[52] U.S. Cl. ................................ 514/384; 548/263; 548/265
[58] Field of Search .............. 548/263, 265; 514/384

[56] References Cited

U.S. PATENT DOCUMENTS 4,082,762 4/1978 Paget et al. ..................... 548/263
4,120,864 10/1978 Seidel et al. .................... 260/308 R

OTHER PUBLICATIONS

Chemical Abstract 76:135847w.
Chemical Abstract 88:170043.
Chemical Abstract 67:38283.
Chemical Abstract 94:65563.
Chemical Abstract 84:44070.
Chemical Abstract 73:36594.
Chemical Abstract 89:215405.
Chemical Abstract 74:99310.
Chemical Abstract 74:111161.
Chemical Abstract 75:146214.
Chemical Abstract 76:85027.
Chemical Abstract 79:104394.
Chemical Abstract 70:37729.
Chemical Abstract 74:141644.
Chemical Abstract 75:98505.
Chemical Abstract 79:66362.
Chemical Abstract 80:54530.
Chemical Abstract 87:15379.
Chemical Abstract 94:39517.
Chemical Abstract 97:79871.
Modi, K. F., et al., J. Indian Chem. Soc., vol. LIV, pp. 741–742 (Jul. 1977).
Lin, Y., et al., J. Heterocyclic Chem., 17, 1077 (1980).

Primary Examiner—Robert T. Bond
Attorney, Agent, or Firm—Vincent L. Fabiano; Stuart R. Suter; Alan D. Lourie

[57] ABSTRACT

Potent dopamine-β-hydroxylase inhibitors having the Formula

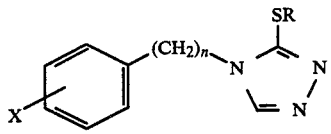

that are useful to inhibit dopamine-β-hydroxylase activity, pharmaceutical compositions including these inhibitors, and methods of using these inhibitors to inhibit dopamine-β-hydroxylase activity in mammals. Also disclosed are novel intermediates useful in preparing the presently invented inhibitors.

21 Claims, No Drawings

DOPAMINE-β-HYDROXYLASE INHIBITORS

FIELD OF THE INVENTION

This invention relates to novel compounds that inhibit dopamine-β-hydroxylase.

BACKGROUND OF THE INVENTION

In the catecholamine biosynthetic pathway, tyrosine is converted in three steps to norephinephrine (NE). Intermediates are dihydroxyphenylalanine (DOPA) and dopamine (DA). Dopamine is hydroxylated to norepinephrine by dopamine-β-hydroxylase (DBH) in the presence of oxygen and ascorbic acid.

Inhibition of catecholamine activity decreases blood pressure. Weinshilboum, *Mayo Clin. Proc.* 55, 39 (1980), reviews compounds that inhibit catecholamine activity by acting upon adrenergic receptors. Alternatively, the catecholamine biosynthetic pathway can be suppressed at any of the three steps, resulting in reduced NE levels. In addition to producing an antihypertensive effect, inhibitors of NE synthesis are active as diuretics, natriuretics, cardiotonics, and vasodilators. Inhibition of DBH activity can have the added advantage of increasing DA levels, which as reported by Ehrreich et al., "New Antihypertensive Drugs," Spectrum Publishing, 1976, pp. 409-432, has selective vasodilator activity at certain concentrations.

DBH inhibitors also have been shown to reduce or prevent formation of gastric ulcers in rats by Hidaka et al., "Catecholamine and Stress," edit. by Usdin et al., Permagon Press, Oxford, 1976, pp. 159-165 and by Osumi et al., *Japan J. Pharmacol.* 23, 904 (1973).

A number of DBH inhibitors are known. These generally are divided into two classes, namely, metal chelating agents, which bind to copper in the enzyme, and phenethylamine analogues. Rosenberg et al., "Essays in Neurochemistry and Neuropharmacology," Vol. 4, edit. by Youdim et al., John Wiley & Sons, 1980, pp. 179-192, and Goldstein, *Pharmacol. Rev.* 18(1), 77 (1966), review DBH inhibitors. The former report that many potent DBH inhibitors have a hydrophobic side chain of size comparable to the aromatic ring of DA, leading the authors to suggest that incorporation of a terminal hydroxyl group on a 4- to 6-carbon side chain on a phenethylamine analogue may yield potent inhibitors.

Known DBH inhibitors include:

(a) 5-alkylpicolinic acids [See, Suda et al., *Chem. Pharm. Bull.* 17, 2377 (1969); Umezawa et al., *Biochem. Pharmacol.* 19, 35 (1969); Hidaka et al., *Mol. Pharmacol.* 9, 172 (1973); Miyano et al., *Chem. Pharm. Bull.* 26, 2328 (1978); Miyano et al., *Heterocycles* 14, 755 (1980); Claxton et al., *Eur. J. Pharmacol.* 37, 179 (1976)];

(b) BRL 8242 [See, Claxton et al., *Eur J. Pharmacol.* 37, 179 (1976)];

(c) 1-alkylimidazole-2-thiols [See, Hanlon et al., *Life Sci.* 12, 417 (1973); Fuller et al., *Adv. Enzyme Regul.* 15, 267 (1976)];

(d) substituted thioureas [See, Johnson et al., *J. Pharmacol. Exp. Ther.* 168, 229 (1969)]; and (e) benzyloxyamine and benzylhydrazine [See, Creveling et al., *Biochim. Biophys. Acta* 64, 125 (1962); Creveling et al., *Biochim. Biophys. Acta* 8, 215 (1962); Van Der Schoot et al., *J. Pharmacol. Exp. Ther.* 141, 74 (1963); Bloom, *Ann. N.Y. Acad. Sci* 107, 878 (1963)].

All the above compounds except benzyloxyamine and benzylhydrazine apparently owe their inhibitory effect to metal chelating properties. Alkyl derivatives of imidazole-2-thiol are more potent, presumably due to non-specific interaction of the alkyl substituent with the enzyme. Benzyloxyamine and benzylhydrazine are phenethylamine analogues which apparently act as competitive inhibitors.

In addition to the above compounds, Runti et al., *Il Farmaco Ed. Sci.* 36, 260 (1980), report that other fusaric acid derivatives and analogues inhibit DBH. These include phenylpicolinic acid, which has twice the inhibitory activity of fusaric acid, and 5-(4-chlorobutyl)picolinic acid, and others such as substituted amides of fusaric acid and acids and amides of 5-butyroylpicolinic acid, 5-aminopicolinic acid and 5-hydrazinopicolinic acid, and derivatives thereof.

Hidaka et al., *Molecular Pharmacology*, 9, 172–177 (1972) report that 5-(3,4-dibromobutyl)picolinic acid and 5-(dimethyldithiocarbamoylmethyl)picolinic acid are DBH inhibitors.

Bupicomide, 5-(n-butyl)picolinamine, is reported by Ehrreich et al., "New Antihypertensive Drugs", Spectrum Publications, 1976, pg. 409-432, to be a DBH inhibitor that has antihypertensive activity.

In European Patent Application No. 125,033 (published Nov. 14, 1984) a series of 1-phenyl and 1-phenylalkylimidazole compounds having a mercapto or alkylthio group in the 2-position are disclosed. These compounds are described as having DBH inhibiting activity.

U.S. Pat. No. 4,487,761 describes several methylpyridine derivatives isolated from the fermentation broth of a strain of Streptoverticillium. These compounds inhibit DBH activity.

U.S. Pat. No. 4,532,331 describes various 1-benzyl-2-aminomethyl imidazole derivatives that inhibit DBH activity and includes pharmaceutical compositions containing these derivatives and methods of using these derivatives to inhibit DBH activity.

Non-specific, often toxic effects of known DBH inhibitors have obviated clinical use of these compounds. Fusaric acid, for example, is hepatotoxic. See, for example, Teresawa et al., *Japan. Cir. J.* 35, 339 (1971) and references cited therein. Presumably, the picolinic acid structure interacts with a number of metalloproteins and enzymes non-specifically to produce the observed side effects.

Compounds structurally related to the presently developed dopamine-β-hydroxylase inhibitors have been synthesized previously. These known compounds include compounds having the formula:

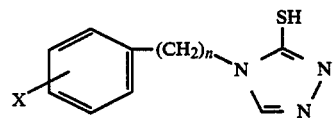

in which:
n is O and X is hydrogen, CH$_3$, OCH$_3$, OCH$_2$CH$_3$, OCH$_2$CH$_2$CH(CH$_3$)$_2$, Br, Cl, I, CF$_3$, NO$_2$, or COOH, or combinations of the above; and
n is 1 and X is hydrogen.
See, e.g., Chem. Abstr. 76:135847w; Chem. Abstr. 88:170043; Chem. Abstr. 67:38283; Chem. Abstr. 94:65563; Chem. Abstr. 84:44070; Chem. Abstr. 73:36594; Chem. Abstr. 89:215405.

Absent from the references disclosing these compounds, however is any suggestion that compounds of the above formula possess activity as dopamine-β-hydroxylase inhibitors or are efficacious in the treatment of diseases, such as hypertension, in which reductions in dopamine-β-hydroxylase activity produce therapeutic benefits. These compounds have been employed as reagents in photographic and electrorecording processes and analytical methods. Also, some of these compounds have been used as fungicides, herbicides, and pesticides. Additionally, certain of these compounds were found to inhibit the growth on mice footpads of leprosy-causing bacteria.

SUMMARY OF THE INVENTION

The present invention resides in the discovery that DBH is inhibited by 4-aralkyl substituted 1,2,4-triazole-3-thiol and 4-aralkyl substituted 1,2,4-triazole-3-alkylthiol compounds. These compounds are potent and produce prolonged DBH inhibition.

Presently preferred compounds of the invention include:
4-(3'-fluorobenzyl)-1,2,4-triazole-3-thiol;
4-(3',5'-difluorobenzyl)-1,2,4-triazole-3-thiol;
4-(3',5'-difluoro-4'-methoxybenzyl)-1,2,4-triazole-3-thiol; and
4-(3',5'-difluoro-4'-hydroxybenzyl)-1,2,4-triazole-3-thiol.

In a further aspect of the invention there are provided novel intermediates useful in preparing 4-aralkyl substituted 1,2,4-triazole-3-thiol and 4-aralkyl substituted 1,2,4-triazole-3-alkylthiol compounds. Each of the intermediates is the N-alkyl substituted phenyl thiosemicarbazone or N-alkyl substituted phenyl thiosemicarbazide of the analogous 4-aralkyl substituted 1,2,4-triazole-3-thiol compound.

The invention also is a method of inhibiting DBH activity in mammals, including humans, which comprises administering internally to a subject an effective amount of a 4-aralkyl substituted 1,2,4 triazole-3-thiol or a 4-aralkyl substituted 1,2,4 triazole-3-alkylthiol compound.

Included in the present invention are pharmaceutical compositions comprising compounds useful in the method of the invention and a pharmaceutical carrier.

DETAILED DESCRIPTION OF THE INVENTION

The presently invented compounds that inhibit DBH have the following formula:

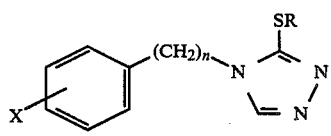
(I)

in which:
n is 0–5;
R is hydrogen or $C_{1-4}$ alkyl; and
X is hydrogen, halo, $C_{1-4}$ alkyl, CN, $NO_2$, $SO_2NH_2$, COOH, CHO, OH, $CH_2OH$, $C_{1-4}$ alkoxy, $CF_3$, $SO_2CH_3$, $SO_2CF_3$, or $CO_2C_aH_{2a+1}$ wherein a is 1–5, or any accessible combination thereof of up to 5 substituents; or
any pharmaceutically acceptable salt or hydrate thereof;

except compounds in which:
n is 0 and X is hydrogen, $CH_3$, $OCH_3$, $OCH_2CH_3$, $OCH_2CH_2CH(CH_3)_2$, Br, Cl, I, $CF_3$, $NO_2$, COOH, or combinations thereof; or
n is 1 and X is hydrogen.

Included in the pharmaceutical compositions of the present invention and employed in the methods of the present invention are compounds having the following formula:

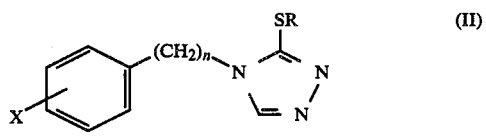
(II)

in which:
n is 0–5;
R is hydrogen or $C_{1-4}$ alkyl; and
X is hydrogen, halo, $C_{1-4}$ alkyl, CN, $NO_2$ $SO_2NH_2$, COOH, CHO, OH, $CH_2OH$, $C_{1-4}$ alkoxy, $CF_3$, $SO_2CH_3$, $SO_2CF_3$, or $CO_2C_aH_{2a+1}$ wherein a is 1–5, or any accessible combination thereof of up to 5 substituents; or
any pharmaceutically acceptable salt or hydrate thereof.

It is intended that Formulae I and II include the tautomer of the compounds in which R is hydrogen, that is, compounds having the above formulae wherein the triazole moiety has either of the below formulae:

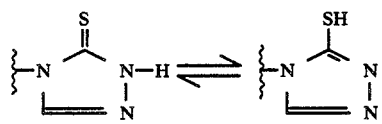

The compounds of Formulae I and II in which n is 1 are prepared from corresponding benzylamines by known processes such as shown in Scheme I, below. The starting benzylamines are known and described in published references or can be obtained readily.

Scheme I illustrates reaction of benzylamines (A) having X substituents, which are the same as X in Formula I, with thiophosgene in the presence of an organic base such as triethylamine to produce substituted benzyl isothiocyanates (B).

From the substituted benzyl isothiocyanates (B), either of two equally desirable synthetic pathways are employed to prepare the 4-aralkyl substituted 1,2,4-triazole-3-thiols (E).

SCHEME I

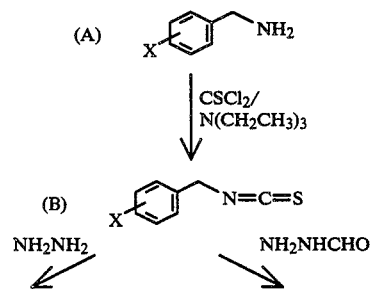

-continued
SCHEME I

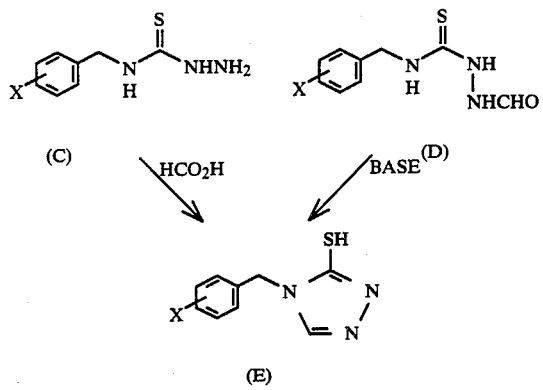

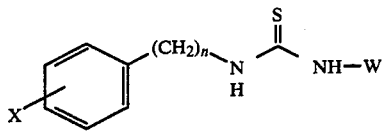

in which:

n is 0 to 5;

X is hydrogen, halo, $C_{1-4}$ alkyl, CN, $NO_2$, $SO_2NH_2$, COOH, CHO, OH, $CH_2OH$, $C_{1-4}$ alkoxy, $CF_3$, $SO_2CH_3$, $SO_2CF_3$, or $CO_2C_aH_{2a+1}$ wherein a is 1–5, or any accessible combination thereof of up to 5 substituents; and W is $NH_2$ or NHCHO;

except compounds in which:

n is O and X is hydrogen, $CH_3$, $OCH_3$, $OCH_2CH_3$, $OCH_2CH_2CH(CH_3)_2$, Br, Cl, I, $CF_3$, $NO_2$, COOH, or combinations thereof; or n is 1 and X is hydrogen.

In one pathway, the substituted benzyl isothiocyanates (B) are reacted with hydrazine hydrate to yield substituted N-benzyl thiosemicarbazones (C). Upon cycloaddition with formic acid, the N-benzyl thiosemicarbazones (C) yield 4-aralkyl substituted 1,2,4-triazole-3-thiols (E). When the other pathway is used, the substituted benzyl isothiocyanates (B) are reacted with formyl hydrazine to produce substituted N-benzyl thiosemicarbazides (D) which, upon cyclization with a base such as an alkoli metal alkoxide, for example sodium ethoxide, yield 4-aralkyl substituted-1,2,4-triazole-3-thiols (E).

Dealkylation of the corresponding 4-alkoxyaralkyl substituted-1,2,4-triazole-3-thiol compounds of Formula (E) with boron tribromide or hydrobromic acid yields the 4-hydroxyaralkyl substituted-1,2,4-triazole-3-thiols of the present invention.

The compounds wherein R is a methyl group are prepared by alkylating corresponding 4-aralkyl substituted-1,2,4-triazole-3-thiols included within the Formula (E) compounds with methyl iodide in methanol by known procedures. Other alkyl halides such as methyl bromide or methyl chloride, in appropriate solvents, can be substituted for methyl iodide. Further, the compounds in which R is an alkyl group other than methyl are prepared by reacting the corresponding 4-aralkyl substituted-1,2,4-triazole-3-thiol of Formula (E) with an alkyl halide, such as butyl iodide, in an appropriate solvent to yield the desired 4-aralkyl substituted-1,2,4-triazole-3-alkylthiol of the present invention.

As illustrated in Scheme I, n is 1; however, n can be from 0 to 5. The compounds wherein n is O are produced by the method of Scheme I, except that the benzylamines (A) are replaced by aniline or substituted anilines. The compounds in which n is 2,3,4, or 5 also are prepared by the Scheme I process, except that the benzylamines (A) are replaced by phenyl $C_{2-5}$ alkylamines such as phenethylamine, 3-phenyl-1-propylamine, or 4-phenyl-1-butylamine.

In preparing the presently invented 4-aralkyl substituted 1,2,4-triazole-3-thiol and 4-aralkyl substituted 1,2,4-triazole-3-alkylthiol compounds, novel intermediate compounds of the following formula are synthesized:

The pharmaceutically acceptable acid addition salts of the compounds of the invention are formed with strong or moderately strong organic or inorganic acids by methods known to the art. For example, the base is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Because the compounds of Formulae I and II inhibit DBH activity, they have therapeutic value as diuretic, natriuretic, cardiotonic, antihypertensive and vasodilator agents, as well as antiulcerogenic agents. Listed in Table I are the compounds of the invention and compounds included in the pharmaceutical compositions of the invention and useful in the methods of the invention that were tested for in vitro DBH inhibition by a standard procedure for assaying conversion of tyramine to octopamine in the presence of DBH. J. J. Pisano, et al., Biochem. Biophys. Acta; 43, 566–568 (1960). Octopamine was assayed following sodium periodate oxidation to p-hydroxybenzaldehyde by measuring spectrophotometric absorbance at 330 nm. In Table I, inhibition is given in molar concentration of compound at which DBH activity was halved ($IC_{50}$). Melting points (mp) are given in °C. Fusaric acid, by this test was found to have an $IC_{50}$ of $8 \times 10^{-7}$M.

TABLE I

| Compound | mp | $IC_{50}$ |
|---|---|---|
| 4-benzyl-1,2,4-triazole-3-thiol | 124–125° | $2.4 \times 10^{-5}$ |
| 4-(3'-fluorobenzyl)-1,2,4-triazole-3-thiol | 124–125° | $2.7 \times 10^{-6}$ |
| 4-(3',5'-difluorobenzyl)-1,2,4-triazole-3-thiol | 129–130° | $1.0 \times 10^{-6}$ |
| 4-(3',5'-difluoro-4'-methoxybenzyl)-1,2,4-triazole-3-thiol | 124–126° | $1.9 \times 10^{-5}$ |
| 4-(3',5'-difluoro-4'-hydroxybenzyl)-1,2,4-triazole-3-thiol | 184–185° | $2.0 \times 10^{-8}$ |

One of the compounds of the invention was tested for its effect in vivo on peripheral dopamine (DA) and norepinephrine (NE) levels substantially by the procedure of DaPrada and Zurcher, Life Sciences, 19, 1161, (1976). Groups of five spontaneously hypertensive rats were dosed orally, twice, the second dose approximately 18 hours after the first, and were sacrificed about 2 hours after the second dose. Averaged results, expressed in micrograms of DA and NE per gram of tissue are given in Table II.

TABLE II

| Compound | DA (μg/g) | NE (μg/g) | DA/NE Ratio |
|---|---|---|---|
| Control (Saline) | 0.314 | 9.98 | 0.0314 |
| Fusaric Acid 50 mg/kg | 0.715* | 8.19 | 0.0875* |
| 4-(3'-fluorobenzyl)-1,2,4-triazole-3-thiol | 0.958* | 8.46 | 0.114* |

*p <.001

Further, spontaneously hypertensive rats were dosed with a suspension or solution of 4-(3'-fluorobenzyl)-1,2,4-triazole-3-thiol at a dose of 50 mg/kg intraperitoneally, and mean arterial blood pressure was monitored for 260 minutes using indwelling cannulae positioned in the tail arteries. When compared to vehicle-treated controls, the tested compound produced statistically significant blood pressure reductions at 60, 140, 160, 200, and 240 minutes after it was administered.

The compounds of Formula II can be incorporated into convenient dosage forms such as capsules, tablets or injectable preparations. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating and compressing, when necessary, for tablet forms, or mixing, filling and dissolving the ingredients, as appropriate, to give the desired oral or parenteral products.

Doses of the present compounds of Formula II in a pharmaceutical dosage unit as described above will be an efficacious, nontoxic quantity selected from the range of 0.1-100 mg/kg of active compound, preferably 0.1-50 mg/kg. The selected dose is administered to a human patient in need of DBH inhibition from 1-6 times daily, orally, rectally, by injection, or continuously by infusion. Oral dosage units for human administration preferably contain from 1 to 500 mg of active compound. Parenteral administration, which uses lower dosages is preferred. Oral administration, at higher dosages, however, also can be used when safe and convenient for the patient.

The method of this invention of inhibiting DBH activity in mammals comprises administering internally to a subject in need of such inhibition an effective DBH inhibiting amount of a compound of Formula II.

The following examples are illustrative of preparation of Formula I compounds. The examples are not intended to limit the scope of the invention as defined hereinabove and as claimed below.

EXAMPLE 1

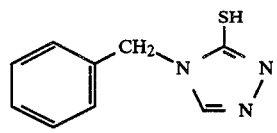

(i) Preparation of benzyl isothiocyanate

A solution of benzylamine (5.4 g, 0.05 mole) and triethylamine (15.4 ml, 0.11 mole) in 50 ml of tetrahydrofuran was added dropwise to a solution of thiophosgene (4.2 ml, 0.055 mole) in 50 ml of tetrahydrofuran with cooling to −10° C. over a period of twenty minutes. The mixture was stirred at 25° C. for 2.75 hours and filtered. The filtrate was treated with charcoal, then filtered and evaporated to an oil. The oil was diluted with hexane:ethyl acetate (90:10) and purified on a flash silica column using hexane:ethyl acetate (90:10) as the eluant to yield benzyl isothiocyanate as a yellow oil.

(ii) Preparation of N-benzyl thiosemicarbazone

A solution of benzyl isothiocyanate (5 g, 33.6 mmole) in ethanol (50 ml) was cooled and stirred at 0° C. during the addition of hydrazine hydrate (1.7 g, 33.6 mmole). The resulting white precipitate was collected by filtration to yield 3.3 g (56%) of N-benzyl thiosemicarbazone, m.p.: 124°-125° C.

(iii) Preparation of 4-benzyl-1,2,4-triazole-3-thiol

Formic acid (6 ml) was heated on a steam bath (15 min.) and N-benzyl thiosemicarbazone (2.2 g, 14.8 mmole) was added. The mixture was heated for an additional hour, then cooled and diluted with water (15 ml). The precipitate was collected by filtration and added to 10% aqueous sodium hydroxide (10 ml). The resulting mixture was heated on a steam bath for one hour, then cooled and acidified with 3N aqueous hydrochloric acid. The product was collected by filtration and recrystallized from ethanol to yield 0.8 g (26%) of 4-benzyl-1,2,4-triazole-3-thiol, m.p.: 124°-125° C.

EXAMPLE 2

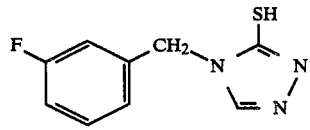

(i) Preparation of 3-fluorobenzyl isothiocyanate

A solution of 3-fluorobenzylamine (6.3 g, 0.05 mole) and triethylamine (15.4 ml, 0.11 mole) in 50 ml of tetrahydrofuran was added dropwise to a solution of thiophosgene (4.2 ml, 0.055 mole) in 50 ml of tetrahydrofuran with cooling to −10° C. over a period of twenty minutes. The mixture was stirred at 25° C. for 2.75 hours and filtered. The filtrate was treated with charcoal, then filtered and evaporated to an oil. The oil was diluted with hexane:ethyl acetate (90:10) and purified on a flash silica column eluted with hexane:ethyl acetate (90:10) to yield 4.3 g (51%) of 3-fluorobenzyl isothiocyanate as a yellow oil.

(ii) Preparation of 4-(3'-fluorobenzyl)-1-formyl-3-thiosemicarbazide

3-Fluorobenzyl isothiocyanate (4.3 g, 25.5 mmole) and formyl hydrazine (1.7 g, 28.7 mole) were refluxed in ethanol (30 ml) for one hour. The reaction mixture was evaporated to dryness, triturated with hexane:ethyl acetate (1:1), filtered, and recrystallized from ethanol-hexane to yield 1.3 g (22%) of crude 4-(3'-fluorobenzyl)-1-formyl-3-thiosemicarbazide.

(iii) Preparation of 4-(3'-fluorobenzyl)-1,2,4-triazole-3-thiol

The crude 4-(3'-fluorobenzyl)-1-formyl-3-thiosemicarbazide (1.3 g) was refluxed overnight in a solution of sodium ethoxide (from sodium (0.3 g) in ethanol (25 ml)). The reaction was filtered, evaporated to dryness, and diluted with water. The aqueous solution was acidified to pH 3-4 with 10% hydrochloric acid, and the precipitate was collected by filtration and recrystallized from ethanol-water to yield 0.5 g (41%) of 4-(3'-fluorobenzyl)-1,2,4-triazole-3-thiol, m.p.: 124°-125° C.

(iv) Preparation of 4-(3'-fluorobenzyl)-1,2,4-triazole-3-thiol hydrochloride

Treatment of 4-(3'-fluorobenzyl)-1,2,4-triazole-3-thiol in ethanolic solution with a solution of hydrogen chloride in diethyl ether yields 4-(3'-fluorobenzyl)-1,2,4-triazole-3-thiol hydrochloride.

EXAMPLE 3

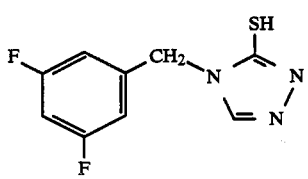

(i) Preparation of 3,5-difluorobenzyl isothiocyanate

A solution of 3,5-difluorobenzylamine (6.5 g, 0.05 mole) and triethylamine (15.4 ml, 0.11 mole) in 50 ml of tetrahydrofuran was added dropwise to a solution of thiophosgene (4.2 ml, 0.055 mole) in 50 ml of tetrahydrofuran with cooling to $-10°$ C. over a period of twenty minutes. The mixture was stirred at 25° C. for 2.75 hours and then filtered. The filtrate was treated with charcoal, filtered, and evaporated to an oil. The oil was diluted with hexane:ethyl acetate (90:10) and purified on a flash silica column eluted with hexane:ethyl acetate (90:10) to yield 8.0 g (62%) of 3,5-difluorobenzyl isothiocyanate as a yellow oil.

(ii) Preparation of 4-(3',5'-difluorobenzyl)-1-formylthiosemicarbazide 3,5-Difluorobenzyl isothiocyanate (9.9 g, 25.5 mmole) and formyl hydrazine (1.7 g, 28.7 mole) were refluxed in ethanol (30 ml) for one hour. The reaction was evaporated to dryness, triturated with hexane:ethyl acetate (1:1), filtered, and recrystallized from ethanol-hexane to yield 3.5 g (35%) of crude 4-(3',5'-difluorobenzyl)-1-formyl-3-thiosemicarbazide.

(iii) Preparation of 4-(3',5'-difluorobenzyl)-1,2,4-triazole-3-thiol

The crude 4-(3',5'-difluorobenzyl)-1-formyl-3-thiosemicarbazide (3.5 g) was refluxed overnight in a solution of sodium ethoxide (from sodium (0.3 g) in ethanol (25 ml.)). The reaction was filtered, evaporated to dryness, and diluted with water. The aqueous solution was acidified to pH 3-4 with 10% hydrochloric acid, and the precipitate was collected by filtration and recrystallized from ethanol-water to yield 2.3 g (71%) of 4-(3',5'-difluorobenzyl)-1,2,4-triazole-3-thiol after recrystallization from water, m.p.: 129°-130° C.

EXAMPLE 4

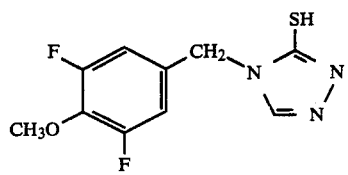

(i) Preparation of 3,5-difluoro-4-methoxybenzyl isothiocyanate

A solution of 3,5-difluoro-4-methoxybenzylamine (8.7 g, 0.05 mole) and triethylamine (15.5 ml, 0.11 mole) in 50 ml of tetrahydrofuran was added dropwise to a solution of thiophosgene (4.2 ml, 0.055 mole) in 50 ml of tetrahydrofuran with cooling to $-10°$ C. over a period of twenty minutes. The mixture was stirred at 25° C. for 2.75 hours and then filtered. The filtrate was treated with charcoal, filtered, and evaporated to an oil. The oil was diluted with hexane:ethyl acetate (90:10) and purified on a flash silica column using hexane:ethyl acetate (90:10) as the eluant to yield 9.2 g (79%) of 3,5-difluoro-4-methoxybenzyl isothiocyanate.

(ii) Preparation of 4-(3',5'-difluoro-4'-methoxybenzyl)-1-formyl-3-thiosemicarbazide 3,5-Difluoro-4-methoxybenzyl isothiocyanate (11.7 g, 25.5 mmole) and formyl hydrazine (1.7 g, 28.7 mole) were refluxed in ethanol (30 ml) for one hour. The reaction was evaporated to dryness, triturated with hexane:ethyl acetate (1:1), filtered, and recrystallized from ethanol-hexane to yield 7.3 g (62%) of crude 4-(3',5'-difluoro-4'-methoxybenzyl)-1-formyl-3-thiosemicarbazide.

(iii) Preparation of 4-(3',5'difluoro-4'-methoxybenzyl)-1,2,4-triazole-3-thiol

The crude 4-(3',5'-difluoro-4'-methoxybenzyl)-1-formyl-3-thiosemicarbazide (7.3 g) was refluxed overnight in a solution of sodium ethoxide (from sodium (0.3 g) in ethanol (25 ml). The reaction was filtered, evaporated to dryness, and diluted with water. The aqueous solution was acidified to pH 3-4 with 10% hydrochloric acid, and the precipitate was collected by filtration and recrystallized from ethanol-hexane to yield 4.4 g (65%) of 4-(3',5'-difluoro-4'-methoxybenzyl)-1,2,4-triazole-3-thiol, m.p.: 124°-126° C.

EXAMPLE 5

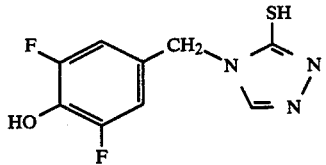

(i) Preparation of 4-(3',5'-difluoro-4'-hydroxybenzyl)-1,2,4-triazole-3-thiol

Boron tribromide (25.6 ml, 0.0408 mole) (40% BBr$_3$ in methylene chloride) was added dropwise over 10 minutes to a suspension of 4-(3',5'-difluoro-4'-methoxybenzyl)-1,2,4-triazole-3-thiol, prepared as in Example 4, (3.3 g) in 50 ml methylene chloride and stirred overnight at 25° C. The reaction mixture was poured into a mixture of ice-ethyl acetate, separated, and extracted two additional times with ethyl acetate. The combined ethyl acetate extracts were washed with brine, dried with sodium sulfate, filtered, and evaporated to an oil. The oil was dissolved in methylene chloride:methanol (90:10) and purified on a flash silica column eluted with methylene chloride:methanol (90:10) to produce a solid which was recrystallized from ethanol-hexane to yield 0.8 g (23%) of 4-(3',5'-difluoro-4'-hydroxybenzyl)-1,2,4-triazole-3-thiol, m.p.: 184°–185° C.

EXAMPLE 6

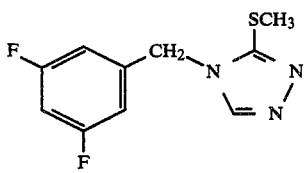

The reaction of 4-(3',5'-difluorobenzyl)-1,2,4-triazole-3-thiol (prepared as in Example 3) with methyl iodide and sodium methoxide in methanol by known techniques yields 4-(3',5'-difluorobenzyl)-3-methylthio-1,2,4-triazole.

EXAMPLE 7

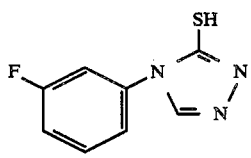

The process of Example 2, beginning with 3-fluoroanaline in place of 3-fluorobenzylamine yields 4-(3'-fluorophenyl)-1,2,4-triazole-3-thiol.

EXAMPLE 8

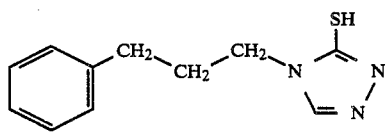

The process of Example 1 beginning with 3-phenyl-1-propylamine in place of benzylamine yields 4-(3'-phenyl-1'-propyl)-1,2,4-triazole-3-thiol.

EXAMPLE 9

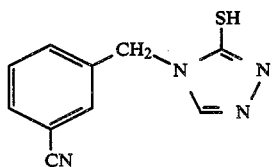

The process of Example 2 beginning with 3-cyanobenzylamine in place of 3-fluorobenzylamine yields 4-(3'-cyanobenzyl)-1,2,4-triazole-3-thiol.

EXAMPLE 10

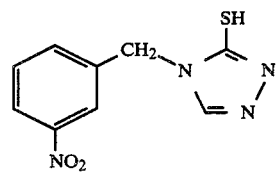

The process of Example 1 beginning with 3-nitrobenzylamine in place of benzylamine yields 4-(3'-nitrobenzyl)-1,2,4-triazole-3-thiol.

EXAMPLE 11

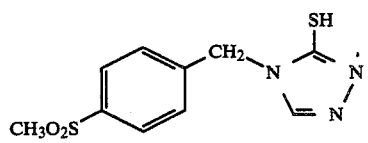

The process of Example 1 beginning with 4-methylsulfonylbenzylamine in place of benzylamine yields 4-(4'-methylsulfonylbenzyl)-1,2,4-triazole-3-thiol.

EXAMPLE 12

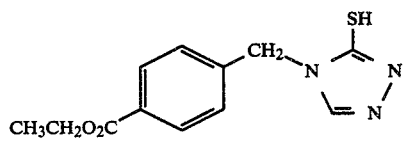

The process of Example 1 beginning with 4-carboethoxybenzylamine in place of benzylamine yields 4-(4'-carboethoxybenzyl)-1,2,4-triazole-3-thiol.

EXAMPLE 13

An oral dosage form for administering the presently invented compounds is produced by screening, mixing, and filling into a hard gelatin capsule the ingredients in Table III, below.

TABLE III

| Ingredients | Amounts |
|---|---|
| 4-(3'-Fluorobenzyl)-1,2,4-triazole-3-thiol | 50 mg |
| magnesium stearate | 5 mg |
| lactose | 75 mg |

EXAMPLE 14

The sucrose, calcium sulfate dihydrate and 4-aralkyl substituted-1,2,4-triazole-3-thiol shown in Table IV below, are mixed and granulated with a 10% gelatin solution. The wet granules are screened, dried, mixed with the starch, talc and stearic acid, screened and compressed into a tablet.

TABLE IV

| Ingredients | Amounts |
|---|---|
| 4-(3',5'-Difluorobenzyl)-1,2,4-triazole-3-thiol | 100 mg |
| calcium sulfate dihydrate | 150 mg |
| sucrose | 20 mg |
| starch | 10 mg |
| talc | 5 mg |
| stearic acid | 3 mg |

EXAMPLE 15

4-(3',5'-Difluoro-4'-hydroxybenzyl)-1,2,4-triazole-3-thiol hydrochloride, 75 mg, is dispursed in 25 ml of normal saline to prepare an injectable preparation.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound represented by the Formula:

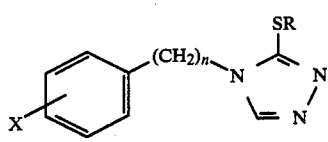

in which:
n is 0–5;
R is hydrogen or $C_{1-4}$ alkyl; and
X is hydrogen, halo, $C_{1-4}$ alkyl, CN, $NO_2$, $SO_2NH_2$, COOH, CHO, $CH_2OH$, OH, $C_{1-4}$ alkoxy, $CF_3$, $SO_2CH_3$, $SO_2CF_3$, or $CO_2C_aH_{2a+1}$ wherein a is 1–5, or any accessible combination thereof of up to 5 substituents; or any pharmaceutically acceptable salt or hydrate thereof;
except compounds in which:
n is 0 and X is hydrogen, $CH_3$, $OCH_3$, $OCH_2CH_3$, $OCH_2CH_2CH(CH_3)_2$, Br, Cl, F, I, $CF_3$, $NO_2$, COOH, or combinations thereof; and
n is 1 and X is hydrogen.

2. A compound according to claim 1 in which:
R is hydrogen.

3. A compound according to claim 2 in which:
n is 1.

4. The compound according to claim 3 that is: 4-(3'-fluorobenzyl)-1,2,4 triazole-3-thiol.

5. The compound according to claim 3 that is: 4-(3',5'-difluorobenzyl)-1,2,4 triazole-3-thiol.

6. The compound according to claim 3 that is: 4-(3',5'-difluoro-4'-methoxybenzyl)-1,2,4 triazole-3-thiol.

7. The compound according to claim 3 that is: 4-(3',5'-difluoro-4'-hydroxybenzyl)-1,2,4 triazole-3-thiol.

8. A pharmaceutical composition in a dosage unit form for inhibiting dopamine-α-hydroxylase activity comprising an effective amount of a compound having the Formula:

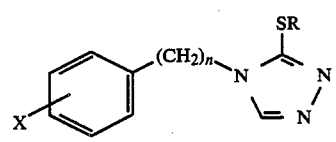

in which:
n is 0–5;
R is hydrogen or $C_{1-4}$ alkyl; and
X is hydrogen, halo, $C_{1-4}$ alkyl, CN, $NO_2$, $SO_2NH_2$, COOH, CHO, $CH_2OH$, OH, $C_{1-4}$ alkoxy, $CF_3$, $SO_2CH_3$, $SO_2CF_3$, or $CO_2C_aH_{2a+1}$ wherein a is 1–5, or any accessible combination thereof of up to five substituents; or any pharmaceutically acceptable salt or hydrate thereof; and
a suitable pharmaceutical carrier.

9. A composition of claim 8 in which the compound is 4-benzyl-1,2,4-triazole-3-thiol.

10. A composition of claim 8 in which the compound is 4-(3'-fluorobenzyl)-1,2,4 triazole-3-thiol.

11. A composition of claim 8 in which the compound is 4-(3',5'-difluorobenzyl)-1,2,4 triazole-3-thiol.

12. A composition of claim 8 in which the compound is 4-(3',5'-difluoro-4'-methoxybenzyl)-1,2,4 triazole-3-thiol.

13. A composition of claim 8 in which the compound is 4-(3',5'-difluoro-4'-hydroxybenzyl)-1,2,4 triazole-3-thiol.

14. A composition of claim 8 containing from 1 to 500 mg of compound per dosage unit.

15. A method of inhibiting dopamine-β-hydroxylase activity in mammals that comprises administering internally to a subject in need of such inhibition an effective amount of a compound having the Formula:

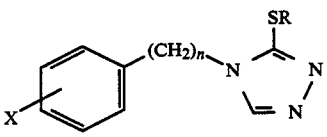

in which:
n is 0–5;
R is hydrogen or $C_{1-4}$ alkyl; and
X is hydrogen, halo, $C_{1-4}$ alkyl, CN, $NO_2$, $SO_2NH_2$, COOH, CHO, $CH_2OH$, OH, $C_{1-4}$ alkoxy, $CF_3$, $SO_2CH_3$, $SO_2CF_3$, or $CO_2C_aH_{2a+1}$ wherein a is 1–5, or any accessible combination thereof of up to five substituents; or any pharmaceutically acceptable salt or hydrate thereof.

16. The method of claim 15 in which the compound is 4-benzyl-1,2,4-triazole-3-thiol.

17. The method of claim 15 in which the compound is 4-(3'-fluorobenzyl)-1,2,4 triazole-3-thiol.

18. The method of claim 15 in which the compound is 4-(3',5'-difluorobenzyl)-1,2,4 triazole-3-thiol.

19. The method of claim 15 in which the compound is 4-(3',5'-difluoro-4'-methoxybenzyl)-1,2,4 triazole-3-thiol.

20. The method of claim 15 in which the compound is 4-(3',5'-difluoro-4'-hydroxybenzyl)-1,2,4 triazole-3-thiol.

21. The method of claim 15 that comprises administering an amount selected from the range of 0.1 to 100 mg per kilogram of compound.

* * * * *